United States Patent
White et al.

(10) Patent No.: US 6,171,234 B1
(45) Date of Patent: Jan. 9, 2001

(54) IMAGING GORE LOADING TOOL

(75) Inventors: David A. White; Linda H. Lammerts van Bueren, both of San Jose, CA (US)

(73) Assignee: SciMed Life Systems, Inc., Maple Grove, MN (US)

(*) Notice: Under 35 U.S.C. 154(b), the term of this patent shall be extended for 0 days.

(21) Appl. No.: 09/161,352

(22) Filed: Sep. 25, 1998

(51) Int. Cl.⁷ .................................................. A61B 1/01
(52) U.S. Cl. .................. 600/102; 604/159; 604/523; 606/108
(58) Field of Search ................................... 600/102, 117; 604/158, 159, 171; 606/108; 226/189, 191

(56) References Cited

U.S. PATENT DOCUMENTS

| | | | |
|---|---|---|---|
| 3,774,605 | * 11/1973 | Jewett | 604/159 |
| 3,835,854 | * 9/1974 | Jewett | 604/159 |
| 4,401,433 | * 8/1983 | Luther | 604/159 |
| 5,201,316 | 4/1993 | Pomeranz et al. | |
| 5,318,541 | * 6/1994 | Viera et al. | 604/159 |
| 5,348,017 | 9/1994 | Thorton et al. | |
| 5,389,100 | * 2/1995 | Bacich et al. | 604/159 |
| 5,503,196 | 4/1996 | Salmon et al. | |
| 5,531,700 | 7/1996 | Moore et al. | |

* cited by examiner

Primary Examiner—John P. Leubecker
(74) Attorney, Agent, or Firm—Townsend and Townsend and Crew LLP

(57) ABSTRACT

A tool for coaxially loading a flexible member into a lumen of a catheter. Typically, the flexible member is a flexible imaging core or similar device. The tool includes a body which has a connector, which connects the body to a hub located on the catheter. A pair of opposed rollers, disposed proximate to the connector, are used to advance the flexible member, through the connector, and into the catheter, which is connected to the connector. The flexible member is advanced by counter rotating the rollers.

21 Claims, 7 Drawing Sheets

Fig. 4
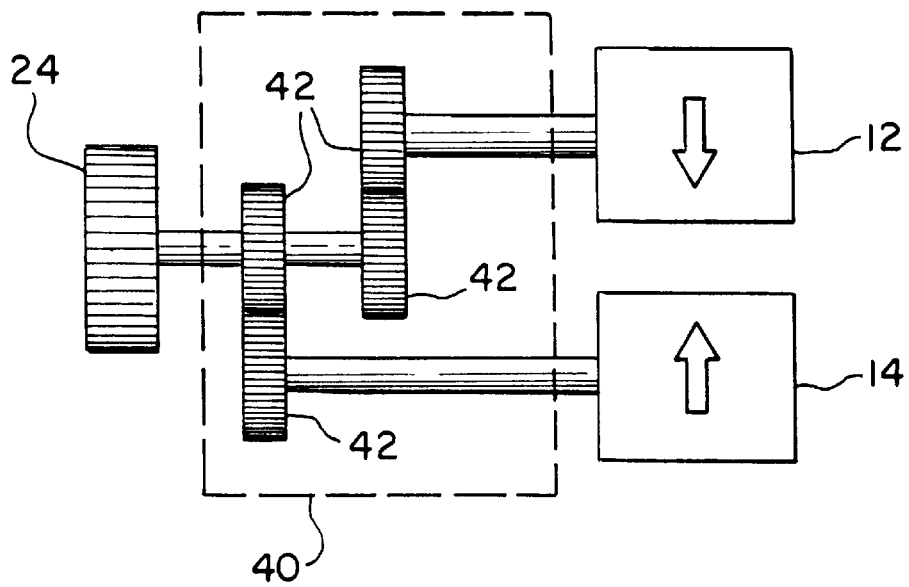
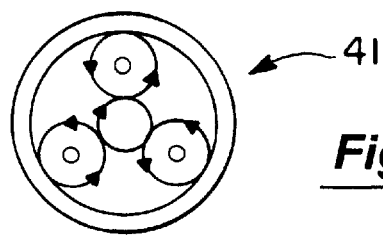
Fig. 4B
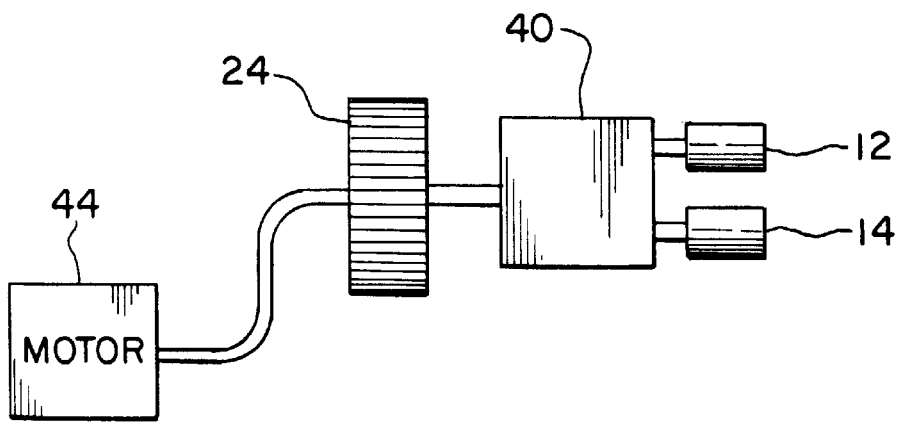
Fig. 4A

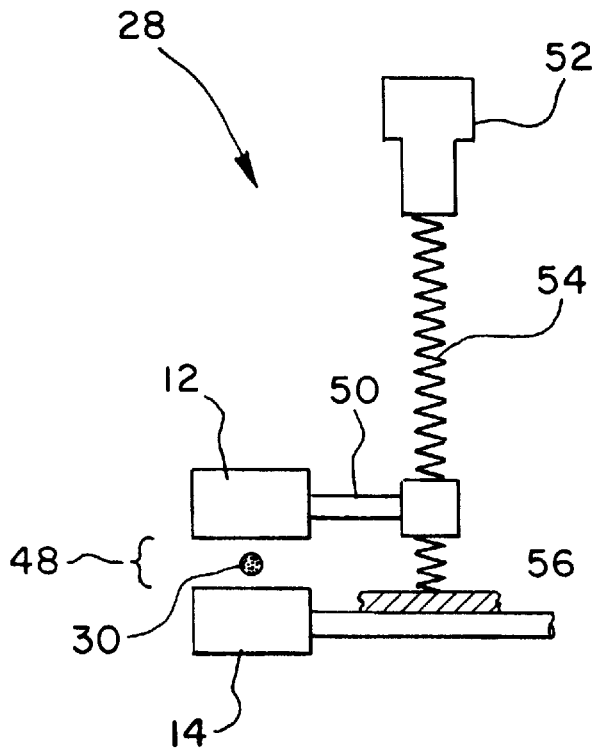
Fig. 5
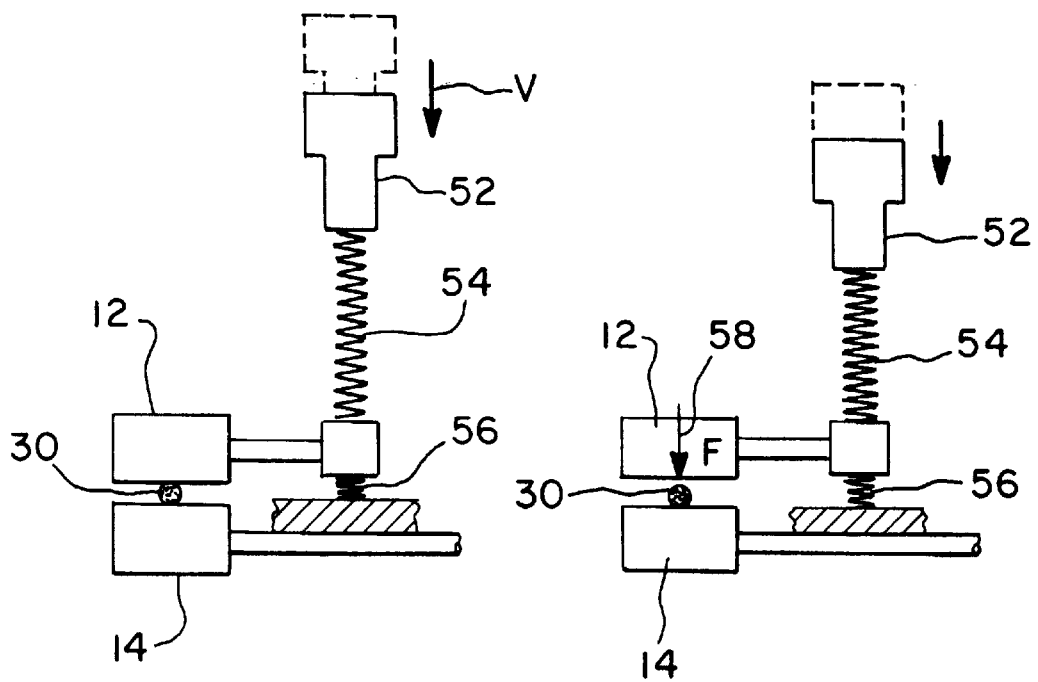
Fig. 5A　　　　Fig. 5B

*Fig. 7*
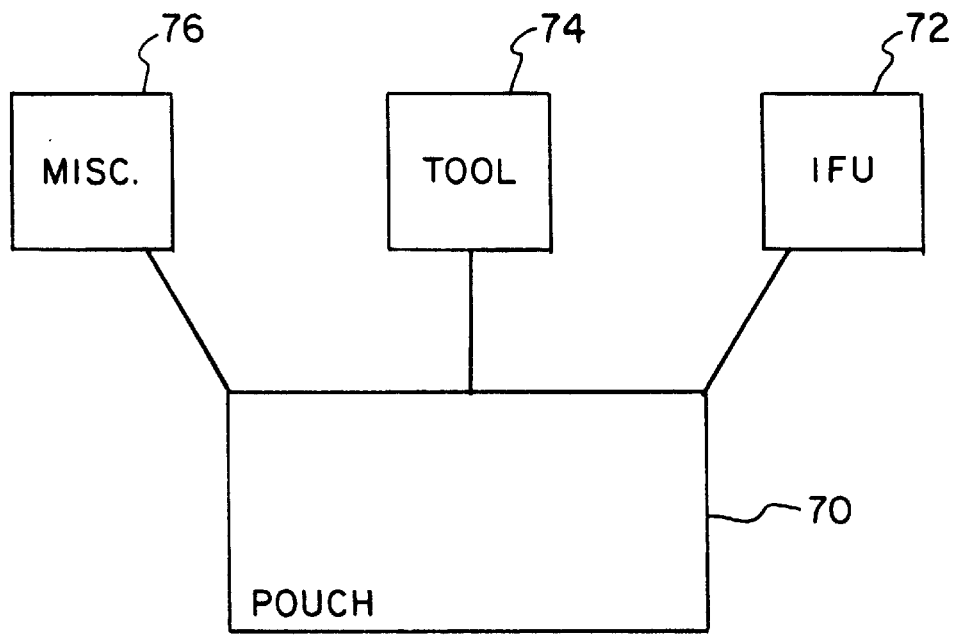
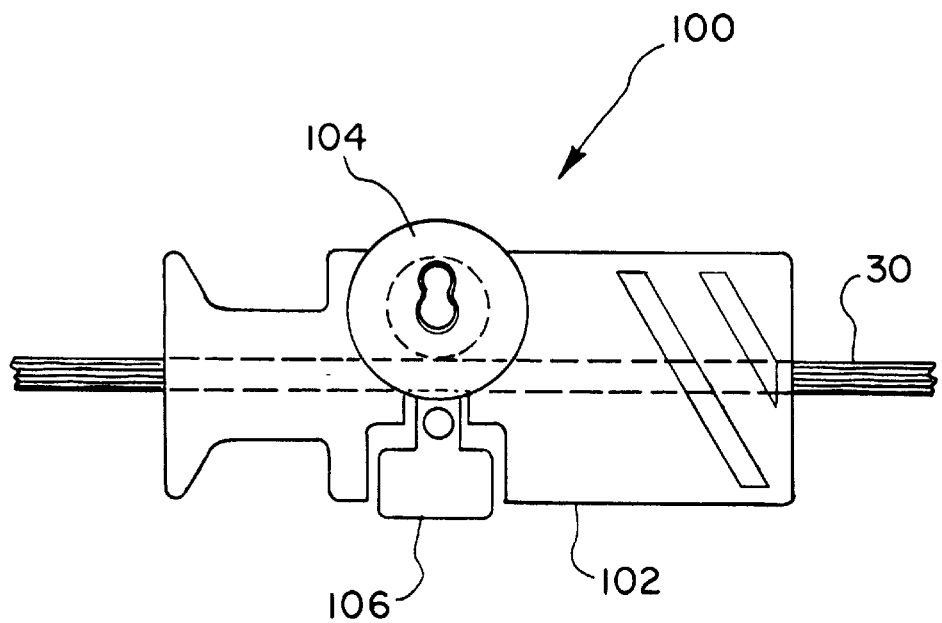
*Fig. 9*

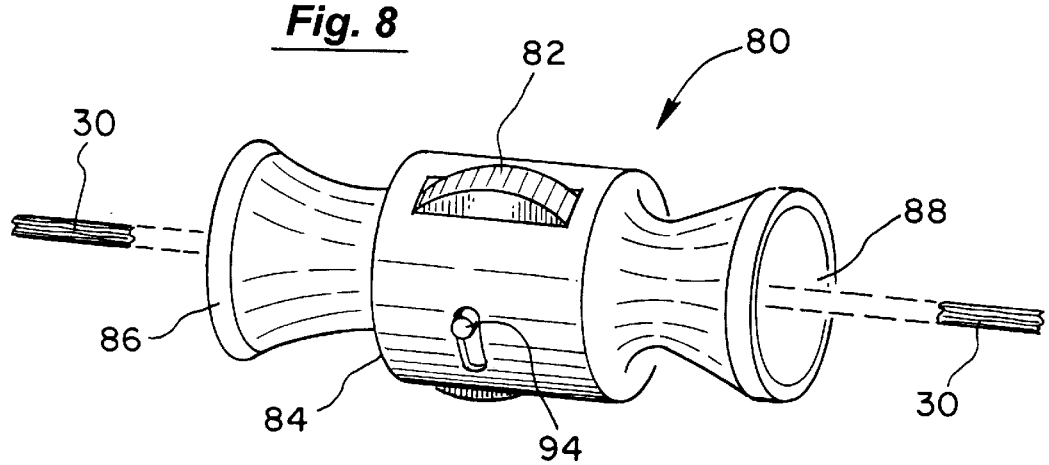
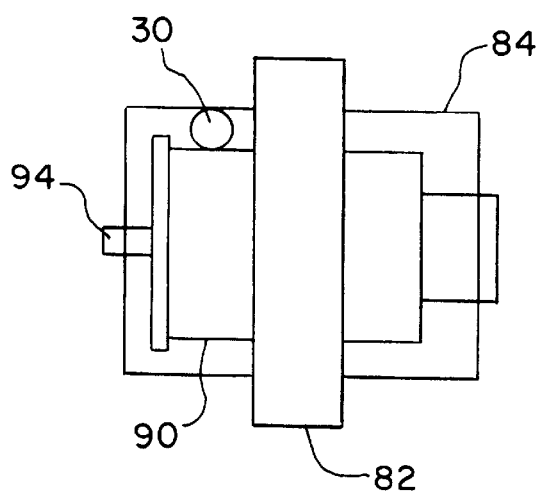
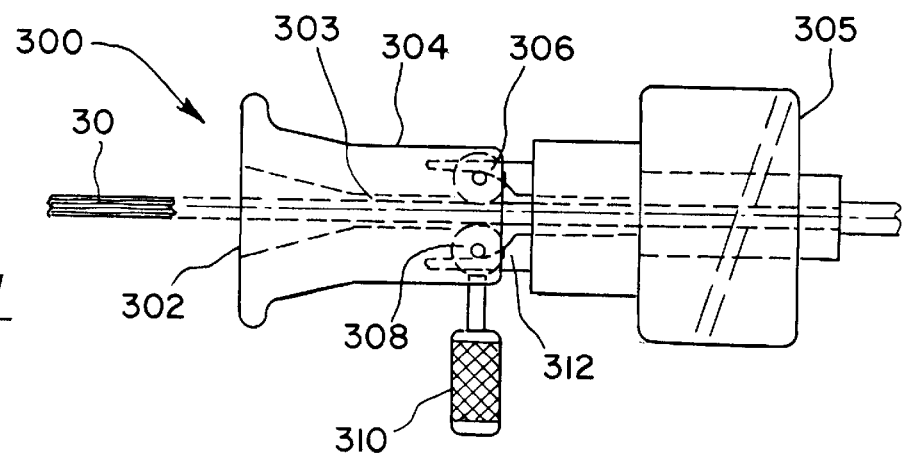

IMAGING CORE LOADING TOOL

BACKGROUND OF THE INVENTION

1. Field of the Invention

The present invention relates generally to medical devices and methods for their fabrication. In particular, the invention relates to a tool for loading a small diameter flexible imaging core into a catheter body.

2. Description of the Relevant Art

Intravascular imaging of blood vessel lesions prior to percutaneous transluminal angioplasty, arthrectomy, and other interventional procedures, is of great benefit. A particularly successful design for an intravascular imaging apparatus employs a rotatable ultrasonic transducer, where the transducer is attached to the distal end of a flexible drive cable or imaging core. The transducer may be disposed within a catheter body or sheath and rotated in order to transmit an ultrasonic signal and produce a video image by well-known techniques.

To be compatible with introduction of the catheter into very small coronary arteries, the imaging core is reduced to correspondingly small diameters. In addition to the small diameter, the drive cable is made highly flexible so that it can pass through tortuous regions of the vasculature, particularly the coronary arteries.

However, as the diameter of the imaging core is reduced, the imaging core tends to lose column strength. Unfortunately, an imaging core with decreased column strength is inclined to collapse or buckle as the imaging core is advanced into the catheter lumen and encounters any type of increased friction due to sharp bends or constrictions, causing the axial load to reach its critical value. This occurrence is problematic since imaging cores are typically loaded into catheters by hand, which means that practitioners must be very precise in order to properly load the imaging core without damaging the imaging core. The problem of loading and advancing the imaging core can be compounded when the imaging core is loaded during clinical use, when the inner lumen of the catheter is typically wet. The surface tension forces present in any fluid on the inner lumenal wall will increase friction, which prevents easy insertion of the imaging core.

For these reasons, it would be desirable to provide a tool for loading a small diameter flexible imaging core having reduced pushability into a catheter body, where use of the tool can reduce bending, kinking, or buckling of the flexible imaging core as the core is advanced into an inner lumen of a catheter body.

SUMMARY OF THE INVENTION

The present invention provides a tool for advancing imaging cores and other elongate flexible members into a lumen of a catheter body. In an exemplary embodiment, the tool facilitates coaxial loading of a small diameter flexible imaging core into an inner lumen of a catheter. The tool attaches to, or is otherwise disposed on, a proximal end of the catheter body into which a flexible member is to be loaded. The tool engages the flexible member and holds the flexible member in axial alignment with the lumen of the catheter body and provides lateral support of the flexible member while advancing the flexible member into the lumen. Preferably, the tool positions the distal end of the flexible member at a point spaced closely to the point of entry into the lumen, for example, usually within 0.5 to 1.5 cm, preferably 1.0 cm or less. By minimizing the distance, buckling, bending, or kinking of the flexible member prior to entry into the catheter body is reduced, which facilitates delivery of the flexible member into a wet or dry catheter body. The tool also allows a practitioner to deliver the imaging core into the catheter faster, more precisely, and more reliably, while avoiding kinking or bending the imaging core or else otherwise damaging the catheter.

In one embodiment, a tool is provided for coaxially loading a flexible member into a lumen of a catheter. Typically, the flexible member is a flexible imaging core or similar device. The tool includes a body which has a connector, which connects the body to a hub located on the catheter. A pair of opposed rollers, disposed proximate to the connector, are used to advance the flexible member, through the connector, and into the catheter, which is connected to the connector. The flexible member is advanced by counter rotating the rollers. Advantageously, a turning device, is used which when rotated causes rotation of at least one of the opposed rollers.

In another embodiment a tool is provided for coaxially loading a flexible imaging core into a lumen of a catheter which has a proximal end and a distal end. The tool has a body, having a connector, which connects to a hub disposed on the proximal end of the catheter. The body further has a first axis and a second axis. A first roller is attached to the first axis and a second roller is attached to the second axis. The flexible imaging core is advanced through the connector and into the catheter, connected to the connector, by counter rotating the rollers.

In another aspect of the invention, a method is provided which includes inserting a flexible imaging core into a tool and advancing the flexible imaging core into a lumen of a catheter.

In yet another aspect of the invention, a method is provided for loading a flexible imaging core into a lumen of a catheter. The method includes inserting a distal end of a flexible imaging core between a pair of opposed rollers; axially aligning the flexible imaging core with a lumen of a catheter; and rotating the rollers to advance the flexible imaging core into the lumen. Preferably, a kit is provided which includes the tool for coaxially loading the imaging core into a lumen of a catheter; instructions for use setting forth the above described method; and a package containing the tool and the instructions for use.

In yet another aspect of the invention, a catheter system is provided which includes a catheter. The catheter has a catheter body, which has a proximal end, a distal end and an inner lumen therebetween. The catheter also has a flexible imaging core, which has a proximal end and a distal end, and which is disposed within the inner lumen. The system also includes a tool which has an advancement mechanism for advancing the flexible imaging core into the inner lumen.

BRIEF DESCRIPTION OF THE DRAWINGS

FIGS. 4 and 4A illustrate a gear train, a component of the loading tool of FIG. 1;

FIG. 5 is a simplified illustration of the regulator assembly according to the present invention;

FIGS. 5A and 5B show the operational performance of the regulator assembly of FIG. 5;

FIG. 7 shows a diagram of components of a kit, which can contain the present invention in FIG. 1 and instructions for its use;

FIG. 8 is a simplified illustration of a tool according to an alternative embodiment of the present invention for coaxially loading a flexible member into a lumen of a catheter;

FIG. 9 is a simplified illustration of a thumbwheel device according to an alternative embodiment of the present invention;

FIG. 11 illustrates yet another alternative embodiment of the present invention.

DESCRIPTION OF THE SPECIFIC EMBODIMENT

The present invention provides for coaxially loading a flexible member into a lumen of a catheter. The present invention can work with any imaging core that incorporates a flexible drive shaft that can be delivered into a catheter body. Specifically, the imaging core will be a small diameter imaging core that has relatively little column strength. The catheter body can include, but is not limited to, ultrasound catheters, angioplasty balloon catheters, radiation catheters, stent delivery catheters, and aneurysm coil delivery catheters.

Figure 1:
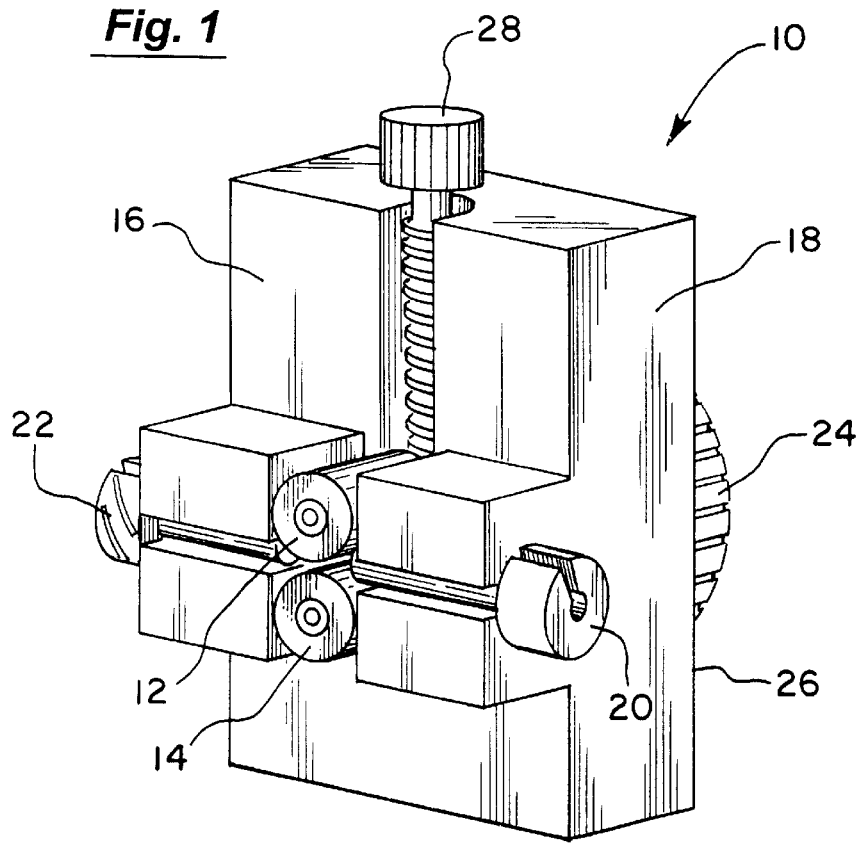
FIG. 1 is a simplified perspective view of an imaging core loading tool according to the present invention.

Referring to FIG. 1, a tool 10 for coaxially loading a flexible member into a lumen of a catheter, is shown according to the present invention. The tool 10 includes a pair of opposed rollers 12 and 14 mounted to a front face 16 of tool body 18, which also has an alignment mechanism 20 and a manifold coupling device 22, which removably receive the inner catheter, and a regulator assembly 28. A turning device 24 is mounted on an opposing face 24 of tool body 16.

Figure 2:
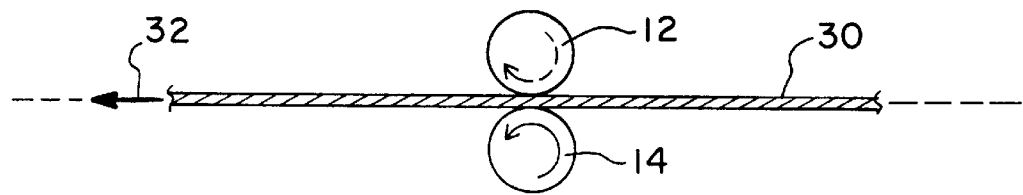
FIG. 2 illustrates the advancing mechanism according to the present invention.

Tool 10 is constructed so that tool body 18 houses roller 12 and roller 14 in an opposed arrangement. The rollers are in close proximity to each and are capable of receiving the imaging core 30 between them. As best illustrated in FIG. 2, rollers 12 and 14 engage imaging core 30 such that a moment applied to rollers 12 and 14 is translated into a force in the direction of a center line 32 of imaging core 30. The force is significant enough to advance imaging core 30 in to, for example, the inner lumen of an intraluminal imaging catheter. Rollers 12 and 14 rotate in opposite directions. The rollers essentially grab the distal end of imaging core 30 and push it forward using the counter-rotating effect provided by the rollers. Because the rollers direct the advancing force to a distal end of imaging core 30, and since the distance between tool 10 and the catheter is short, the imaging core is prevented from kinking or bending.

Once imaging core 30 is placed into tool 10, the rollers apply a compressive force into imaging core 30. Once the compressive force is applied, at least one of the rollers 12 and 14 are made to rotate. Preferably, the rollers rotate in opposite directions which causes imaging core 30 to be advanced. Rollers 12 and 14 are soft, pliable rollers. Preferably, they are made of rubber or similarly resilient material.

Figure 3:
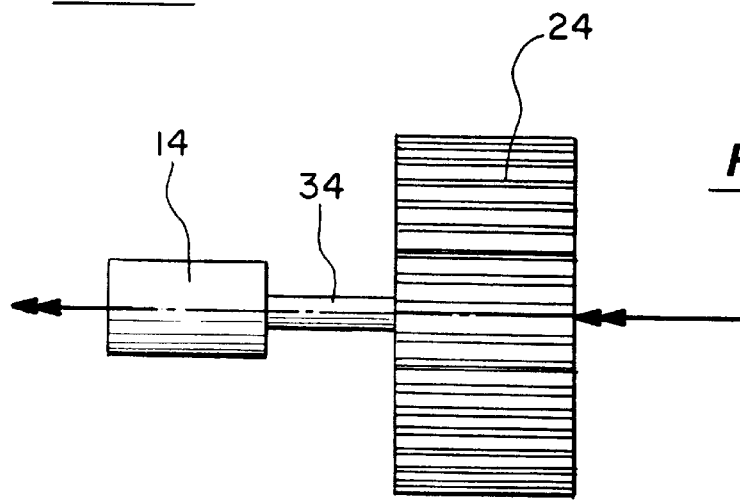
FIG. 3 illustrates a turning device and roller, components of the loading tool of FIG. 1.

Rollers 12 or 14 can be made to rotate using essentially any motive force. For example, the rotation can be caused using hand/finger force or (electro)motor force applied to turning device 24. Preferably, to provide adequate feedback, turning device 24 is turned by hand. Turning device 24 is shown on the back face 26 of tool body 18. Turning device 24 can be molded or machined and made from any type of plastic or metal. The device is large enough to accommodate the human hand. As illustrated in FIG. 3, turning device 24 has a common axis 34 to which roller 14 and turning device 24 are both attached. As can be understood from the figure, rotation of turning device 24 will cause roller 14 to rotate in a corresponding speed and direction.

In an alternative embodiment, illustrated in FIGS. 4 and 4A, roller 14 can be connected to a gear train 40 which allows for timely delivery of imaging core 30. Gear train 40 is made up of an assortment of gears 42 which can be combined to increase or decrease the rotation rate of rollers 12 and 14, relative to the driving force. In an alternative embodiment, shown in FIG. 4B, a planetary gear train 41 is used to advance the imaging core. The gears may be directly or indirectly in contact with the imaging core. A motor 44 can also be used to rotate turning device 24. Motor 44 is housed inside or mounted externally to tool body 18, or supplied as a separate unit. Other driving mechanisms can include, but are not limited to, a thumb wheel, a geared rip cord, a wind-up spring mechanism, a hand crank, or similar devices.

Roller 12 can freely rotate about an axis and need not be driven. Although roller 12 is not affirmatively rotated in the preferred embodiment, the position of the axis of rotation of roller 12 can be adjusted in the vertical direction. As illustrated in FIGS. 5, 5A, and 5B, regulator assembly 28 includes two biasing members 54 and 56, which are preferably coil springs, but can be any suitable spring-like material. First spring 54 and second spring 56 each have a proximal end and a distal end. The proximal end of first spring 54 is coupled to drive mechanism 52 and the distal end is attached to shaft 50, which defines the axis of rotation for roller 12. The proximal end of spring 56 is coupled to shaft 50 and the distal end is attached to tool body 18. Springs 54 and 56 are compressed and released by applying a vertical force V to the spring combination through mechanical drive mechanism 52.

Initially, a gap 48 will exist between rollers 12 and 14 when there is no force V being applied to spring combination 54 and 56. Gap 48 is of a suitable dimension to place and remove imaging core 30. When imaging core 30 is placed between rollers 12 and 14, gap 48 can be reduced, by compressing first and second springs 54 and 56 until both rollers touch on imaging core 30, using drive mechanism 52. When rollers 12 and 14 touch imaging core 30, force 58, which acts to press the rollers onto the imaging core 30, can be increased by applying more compression to first spring 54 by screwing down screw 52. The compression will provide an increase in the friction between rollers 12 and 14 and imaging core 30, thereby further facilitating advancement of imaging core 30. By releasing or unscrewing screw 52, shaft 50 will move upward to an initial position, once again creating gap 48, due to the decompression of second spring 56. Drive mechanism 52 is preferably a screw that can be rotated into and out of tool body 18, but can be any suitable linear drive mechanism, such as a pneumatic actuator or solenoid.

Figure 6:
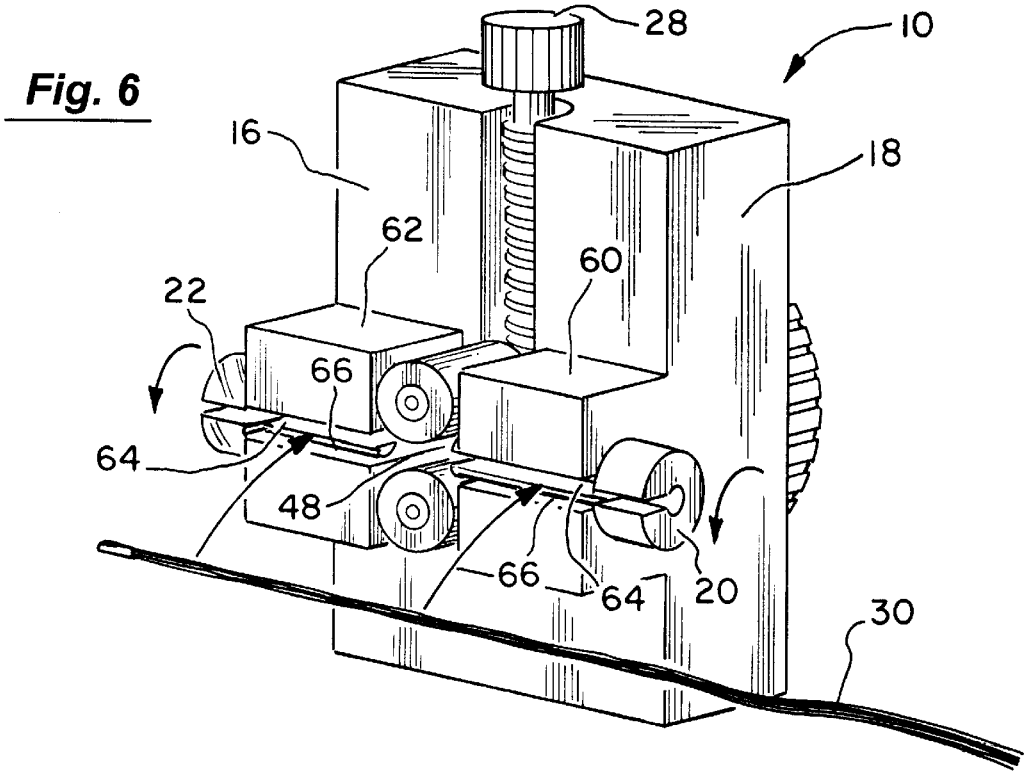
FIGS. 6 and 6A are simplified illustrations of the alignment device and manifold coupling device according to the present invention.
Figure 6A:
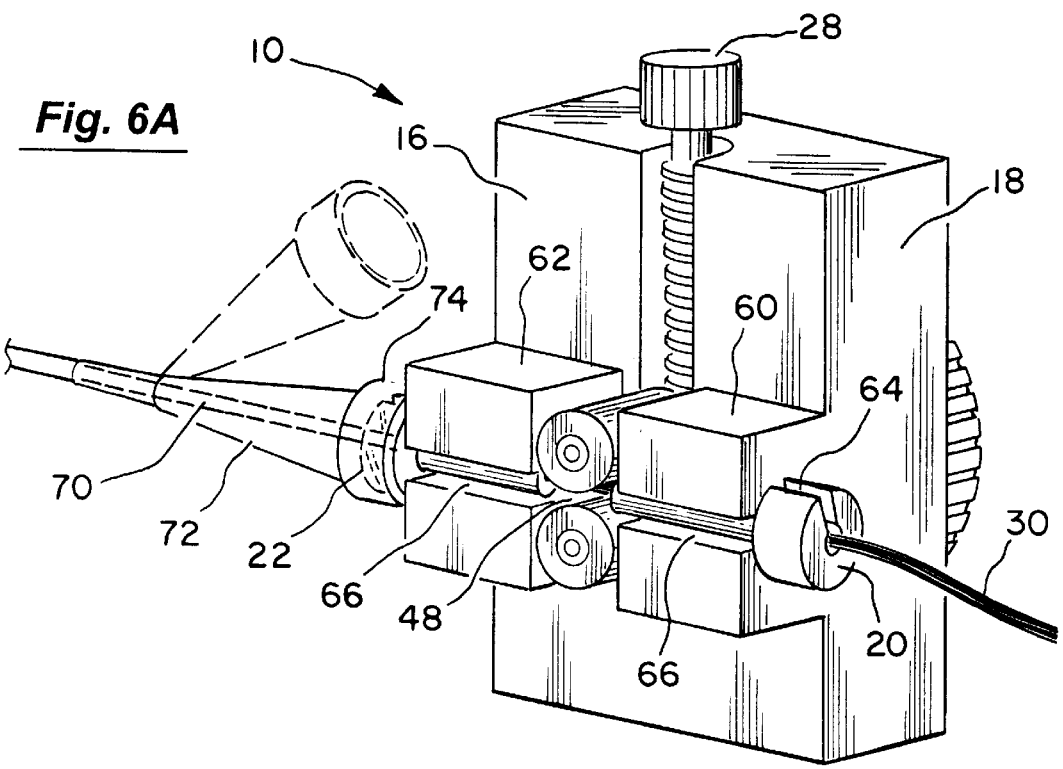

Referring now to FIGS. 6 and 6A, in an exemplary embodiment, tool body 18 is shown with first mount 60 and second mount 62. Mounts 60 and 62 extend from front face 16 of tool body 10 and have slots 66 that align with gap 48. According to the invention, alignment device 20 is shown inserted into first mount 60 and manifold coupling device is shown mounted into second mount 62. Both alignment device 20 and manifold coupling device 22 have slots 64, which can be turned to align with slots 66. When slots 64 are aligned with mount slots 66 imaging core 30 can be loaded into mounts 60 and 62 and between rollers 12 and 14. In this manner, imaging core 30 is kept substantially in the center of rollers 12 and 14. Imaging core 30 is substantially locked into position by turning alignment device 20 and manifold coupling device 22 at least 90° from their loading position.

Once imaging core 30 is in place, the distal end of imaging core 30 can be inserted into an inner lumen 70 of a catheter body 72. Catheter body 72 is attached to tool 10 at connector 74 which is attached to the end of manifold coupling device 22. Once catheter body 72 is connected to tool body 10, the inner lumen 70 is in direct alignment with the distal end of imaging core 30. The effective distance of travel for the distal end of imaging core 30 and the inner lumen is typically less than 1 cm. Connector 74 can be any suitable connecting device, but preferably is a Luer connector.

Imaging core 30 is in position to be advanced into inner lumen 70 by rollers 12 and 14. At the end, the proximal end of imaging core 30 can be removed by unscrewing regulator assembly 28 and releasing rollers 12 and 14. Alignment device 20 and manifold coupling device 22 are counter-rotated to again align slots 64 and mount slots 66. Tool 10 can then be taken to the side, while the remainder of the imaging core is advanced manually and completely into the inner lumen of the catheter body.

Referring now to FIG. 7, which shows a pouch 70 which may contain the tool 74 as described above, instructions 72 for using tool 74, and other miscellaneous components 76, which may also be contained in the kit.

Referring now to FIG. 8, tool 80, for coaxially loading a flexible member into a lumen of a catheter, is shown according to an alternative embodiment of the present invention. The tool 80 includes a thumbwheel 82 disposed in tool body 84, which has an alignment mechanism 86 and a coupling device 88, which removably receive the flexible imaging core 30. As can be best understood in FIG.8A, imaging core 30 is inserted into alignment mechanism 86 until it is positioned between inner roller 90 and an inner portion of tool body 84. Once imaging core 30 is in place, a release button 94, disposed on an outer portion of tool body 84 can be released to allow inner roller 90 to contact imaging core 30 and effectively holding it in place. Once imaging core 30 is held in position, the distal end of imaging core 30 can be inserted into an inner lumen of a catheter body. The catheter body is attached to tool 80 at coupling device 88, which causes the inner lumen to be in direct alignment with the distal end of imaging core 30. Imaging core 30 is then advanced into inner lumen by causing thumbwheel 82 to rotate.

In yet another alternative embodiment, as shown in FIG. 9, a thumbwheel device 100 is used which has a tool body 102 with a thumbwheel 104 disposed therein. Release button 106 is integrated into tool body 102. When activated, release button 106 causes a force to be applied directly to imaging core 30, forcing it into contact with thumbwheel 104. In this embodiment, thumbwheel 104 is set in-line with imaging core 30, such that as thumbwheel 104 is rotated, imaging core 30 can be advanced.

Figure 10A:
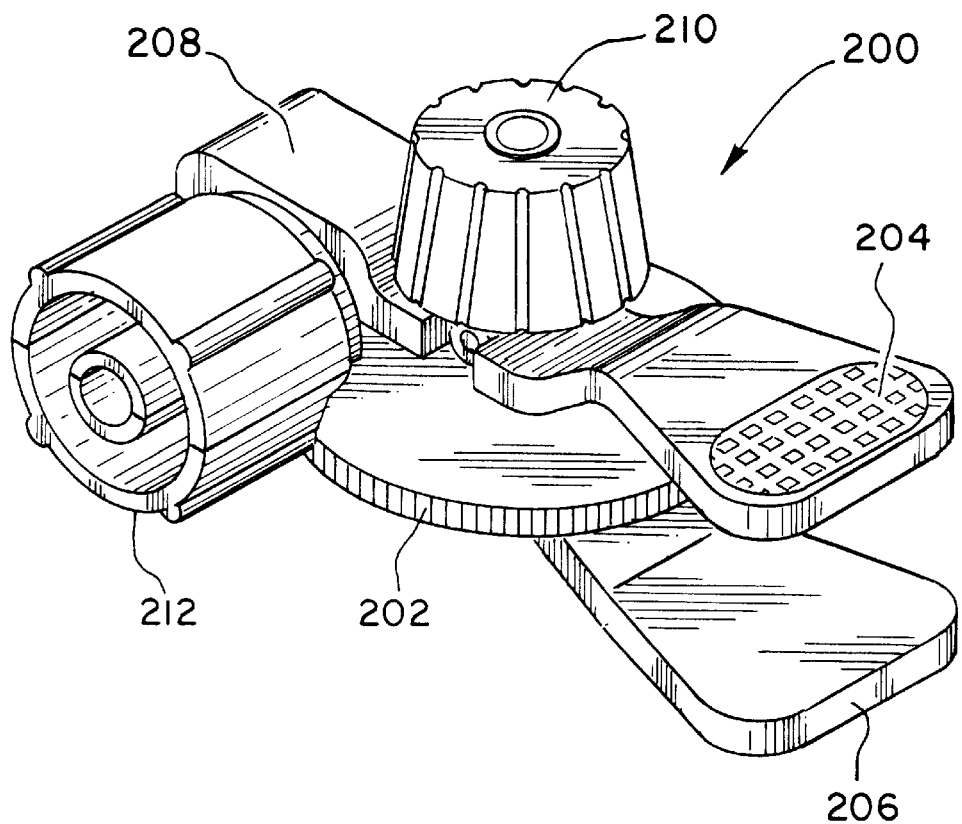
FIGS. 10A and 10B illustrate an alternative method for inserting and advancing an imaging core according to an alternative embodiment of the present invention.
Figure 10B:
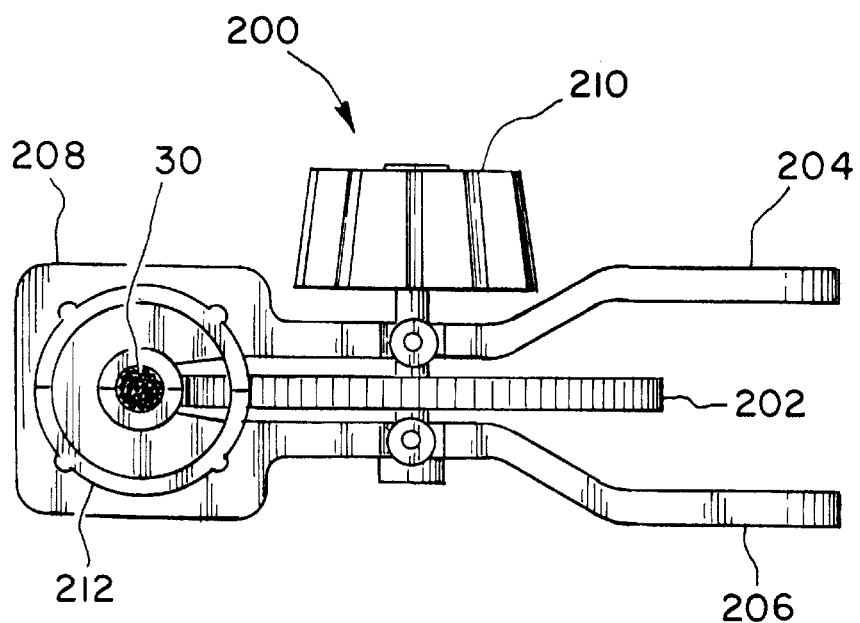

Regarding FIGS. 10A and 10B, an alternative method for inserting imaging core 30 into the tool and advancing the imaging core, is illustrated. Loading tool 200 includes a drive wheel 202 and levers 204 and 206. When levers 204 and 206 are compressed, the tool opens and imaging core 30 can be inserted into alignment mechanism 208. When levers 204 and 206 are released, alignment mechanism 208 clamps onto imaging core 30 and holds the imaging core firmly in alignment mechanism 208. Turning knob 210 causes drive wheel 202 to rotate. Since imaging core is in contact with drive wheel 202, imaging core 30 can be linearly advanced into an inner lumen of a catheter body connected at coupler 212.

FIG. 11, illustrates yet another alternative embodiment of the present invention. Loading tool 300 works primarily along the same principles as do the other embodiments described above. In this embodiment, imaging core 30 is manually inserted into end 302 of tool body 304, until the imaging core reaches a position in passage 303 between oppositely disposed rollers 306 and 308. While in passage 303, imaging core 30 is in alignment with an inner lumen of a catheter body, which may be coupled to coupler 305. Turning mechanism 310 is manually pushed into tool body 304, to force lever 312 to push roller 306 against imaging core 30 until the imaging core is held firmly between rollers 306 and 308. Turning mechanism 310 is then locked in position. Rotating tuning mechanism 310 causes imaging core 30 to be advanced into the inner lumen of the catheter body.

Alternatives and substitutions will be apparent to persons of skill in the art. Accordingly, the invention is not intended to be limited except as provided by the appended claims.

What is claimed is:

1. A tool for coaxially loading a flexible member into a lumen of a catheter, said tool comprising:
   a frame having a connector which connects to a hub on a catheter;
   at least one roller disposed on the frame proximate to the connector so that a flexible member, in use, may be advanced through the connector and into the catheter when connected to the connector by rotating the roller; and
   a regulator assembly for adjusting a position of the at least one roller along a translational path relative to the frame.

2. The tool of claim 1, further comprising a turning mechanism, wherein rotation of the turning mechanism causes rotation of the at least one roller.

3. The tool of claim 1, wherein the at least one roller comprises a pair of opposed rollers, wherein said opposed rollers are counter rotated to advance the flexible member.

4. The tool of claim 1, in which the regulator assembly comprises:
   a mechanical drive mechanism; and
   a pair of opposed biasing members operatively coupled to said mechanical drive mechanism, wherein said mechanical drive mechanism operates on said pair of biasing members to move the at least one roller from a first position to a second position.

5. The tool of claim 1, wherein the frame and the at least one roller are configured for coaxially loading a flexible member in the form of a flexible imaging core into the lumen of the catheter.

6. The tool of claim 1, further comprising an alignment device having a slot for removably receiving said flexible member, said slot, in use, being substantially aligned with the inner lumen of the catheter when the catheter is connected to said connector.

7. The tool of claim 1, further comprising a manifold coupling device having a slot for removably receiving said flexible member, said slot, in use, being in direct alignment with the inner lumen of the catheter when the catheter is connected to said connector.

8. The tool of claim 1, wherein the at least one roller is movable between a first position and a second position.

9. A tool for coaxially loading a flexible imaging core into an inner lumen of a catheter having a proximal end and a distal end, said tool comprising:

a body having a connector for connection to a hub disposed on the proximal end of a catheter, said body having a first axis and a second axis;

a first roller attached to the first axis;

a second roller attached to the second axis;

wherein, in use, the flexible imaging core is advanced through said connector and into the catheter, when the catheter is connected, to the connector by counter rotating the rollers; and a regulator assembly for adjusting a position of one of the rollers along a translational path relative to the other of the rollers.

10. The tool of claim 9, further comprising a turning device attached to said first axis, wherein rotation of the turning device causes said first axis and said first roller to rotate.

11. The tool of claim 9, in which the regulator assembly comprises:

a mechanical drive mechanism; and a pair of opposed biasing members operatively coupled to said mechanical drive mechanism, wherein said mechanical drive mechanism engages said pair of biasing members to move said second axis from a first position to a second position.

12. The tool of claim 9, further comprising an alignment device having a slot for removably receiving said imaging core, said slot, in use, being substantially aligned with the inner lumen of the catheter when the catheter is connected to said connector.

13. The tool of claim 9, further comprising a manifold coupling device having a slot for removably receiving said imaging core, said slot, in use, being in direct alignment with the inner lumen of the catheter when the catheter is connected to said connector.

14. A method comprising:

inserting a flexible member into a tool having a linear path capable of receiving a flexible member;

displacing a driver disposed on said tool along a translational path when said flexible member is in said linear path thereby to engage said flexible member with said driver; and advancing said flexible member into a lumen of a catheter.

15. A method for loading a flexible imaging core into a lumen of a catheter, said method comprising:

inserting a distal end of a flexible imaging core between a pair of opposed rollers;

axially aligning said flexible imaging core with a lumen;

displacing one of the rollers along a translational path relative to the other of said rollers to engage the flexible imaging core between the rollers; and rotating said rollers to advance the flexible imaging core into said lumen.

16. A catheter system comprising:

a catheter comprising a catheter body having a proximal end, a distal end and an inner lumen therebetween;

a flexible imaging core, having a proximal and a distal end, disposed within the inner lumen; and a tool having an advancement mechanism for advancing said flexible imaging core into said inner lumen, said advancing mechanism comprising at least one roller mounted for adjustment along a translational path.

17. The catheter system as in claim 16, wherein the catheter further comprises a hub secured on the proximal end of the catheter; wherein said tool has a connector which connects to the hub so that the imaging core may be advanced through the connector and into the inner lumen of said catheter connected to the connector.

18. A tool for coaxially loading a flexible member into a lumen of a catheter, said tool comprising:

a frame having a linear path capable of receiving a flexible member;

a connector on the frame at an end of the path, said connector being releasably connectable to a hub on the catheter so as to hold the catheter such that the lumen of the catheter is aligned with the path;

a driver on the frame along the path, said driver being engageable with the flexible member when said member is in the path; and a regulator assembly for adjusting a position of the driver along a translational path relative to the frame so as, in use to engage the flexible member when received in the linear path.

19. The tool as in claim 18, wherein the end of the path is at a distance of 1.0 cm or less from an entry point of said lumen.

20. A tool for coaxially loading a flexible member into a lumen of a catheter, said tool comprising:

a frame having a connector which connects to a hub on a catheter;

at least one roller disposed on the frame proximate to the connector so that a flexible member may be advanced through the connector and into the catheter when connected to the connector, by rotating the roller; and a regulator assembly comprising:

a mechanical drive mechanism; and a pair of opposed biasing members operatively coupled to said mechanical drive mechanism, wherein said mechanical drive mechanism operates on said pair of biasing members to move the at least one roller from a first position to a second position.

21. A tool for coaxially loading a flexible imaging core into an inner lumen of a catheter having a proximal end and a distal end, said tool comprising:

a body having a connector for connection to a hub disposed on the proximal end of a catheter, said body having a first axis and a second axis;

a first roller attached to the first axis;

a second roller attached to the second axis;

wherein, in use, said flexible imaging core is advanced through the connector and into the catheter when connected to the connector by counter rotating the rollers; and a regulator assembly comprising:

a mechanical drive mechanism; and a pair of opposed biasing members operatively coupled to said mechanical drive mechanism, wherein said mechanical drive mechanism engages said pair of biasing members to move said second axis from a first position to a second position.

* * * * *